(12) United States Patent
Lawter et al.

(10) Patent No.: US 6,682,348 B2
(45) Date of Patent: Jan. 27, 2004

(54) DISPENSING APPARATUS AND CARTRIDGE

(75) Inventors: James R. Lawter, Yardley, PA (US); Michael G. Lanzilotti, Newtown, PA (US); Mark Bates, Westwood, MA (US); Gregory H. Hunter, Dover, MA (US)

(73) Assignee: OraPharma, Inc., Warminster, PA (US)

( * ) Notice: Subject to any disclaimer, the term of this patent is extended or adjusted under 35 U.S.C. 154(b) by 0 days.

(21) Appl. No.: 10/112,450

(22) Filed: Mar. 29, 2002

(65) Prior Publication Data

US 2003/0186191 A1 Oct. 2, 2003

(51) Int. Cl.[7] .............................................. A61C 5/04
(52) U.S. Cl. .................................. 433/90; 604/218
(58) Field of Search .......................... 433/90, 89, 80; 222/327, 326, 386; 604/218, 232, 235

(56) References Cited

U.S. PATENT DOCUMENTS

| | | | |
|---|---|---|---|
| 4,175,326 A | | 11/1979 | Goodson |
| 5,000,886 A | | 3/1991 | Lawter et al. |
| 5,112,307 A | * | 5/1992 | Haber et al. ................. 604/110 |
| 5,143,661 A | | 9/1992 | Lawter et al. |
| 5,236,355 A | | 8/1993 | Brizzolara et al. |
| 5,366,733 A | | 11/1994 | Brizzolara et al. |
| 5,500,228 A | | 3/1996 | Lawter et al. |
| 5,622,498 A | | 4/1997 | Brizzolara et al. |
| 5,871,355 A | * | 2/1999 | Dragan et al. ................. 433/90 |
| 6,083,002 A | * | 7/2000 | Martin et al. .................. 433/90 |
| RE37,439 E | * | 11/2001 | Firth et al. .................... 604/110 |

* cited by examiner

Primary Examiner—Todd E. Manahan
Assistant Examiner—Melba Bumgarner
(74) Attorney, Agent, or Firm—Holland & Knight LLP

(57) ABSTRACT

A device for the treatment of periodontal disease includes a handle that has a configuration familiar to dental professionals, and a cartridge, that is locked into the handle when use, typically delivery of a composition to a periodontal pocket is desired. The cartridge provides for effective delivery of compositions, such as agents, as its tip is deformable, typically from a circular to an oval shape so as to flatten. The deformation may be made, either manually, by the dental professional, or upon contact with teeth or other tissues, whereby this flattened tip can penetrate deeply into periodontal pockets for quick and direct application of the composition, for example, therapeutic agents.

44 Claims, 12 Drawing Sheets

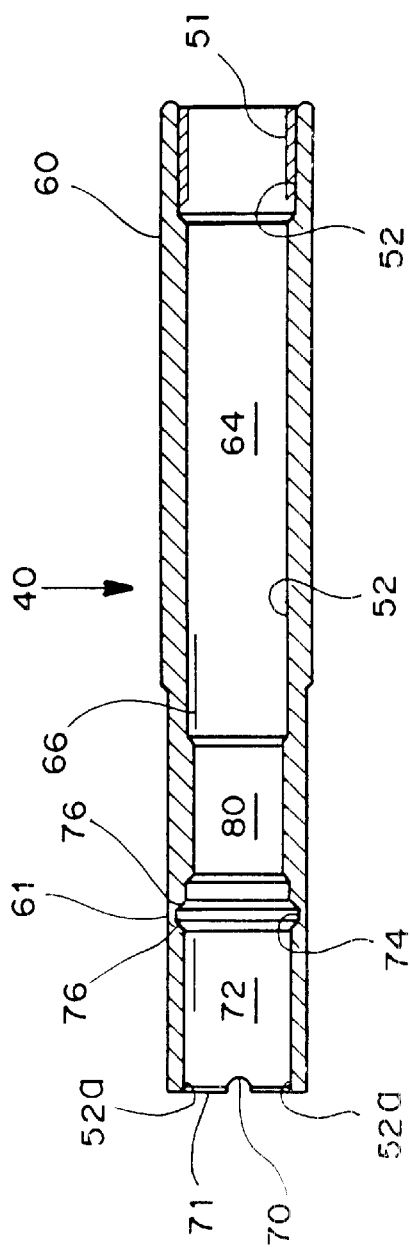
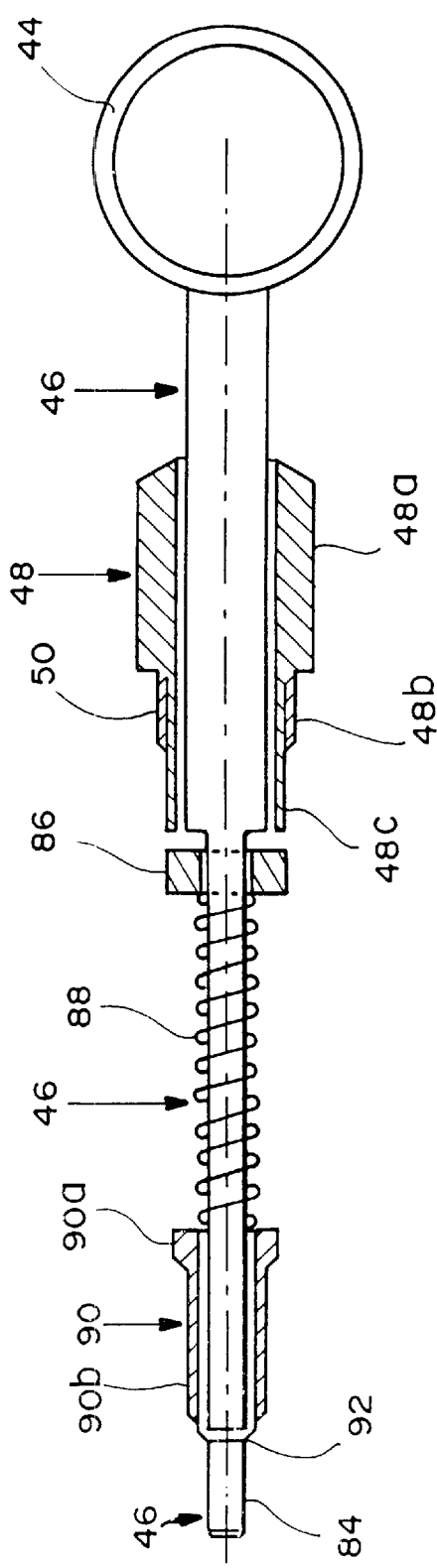

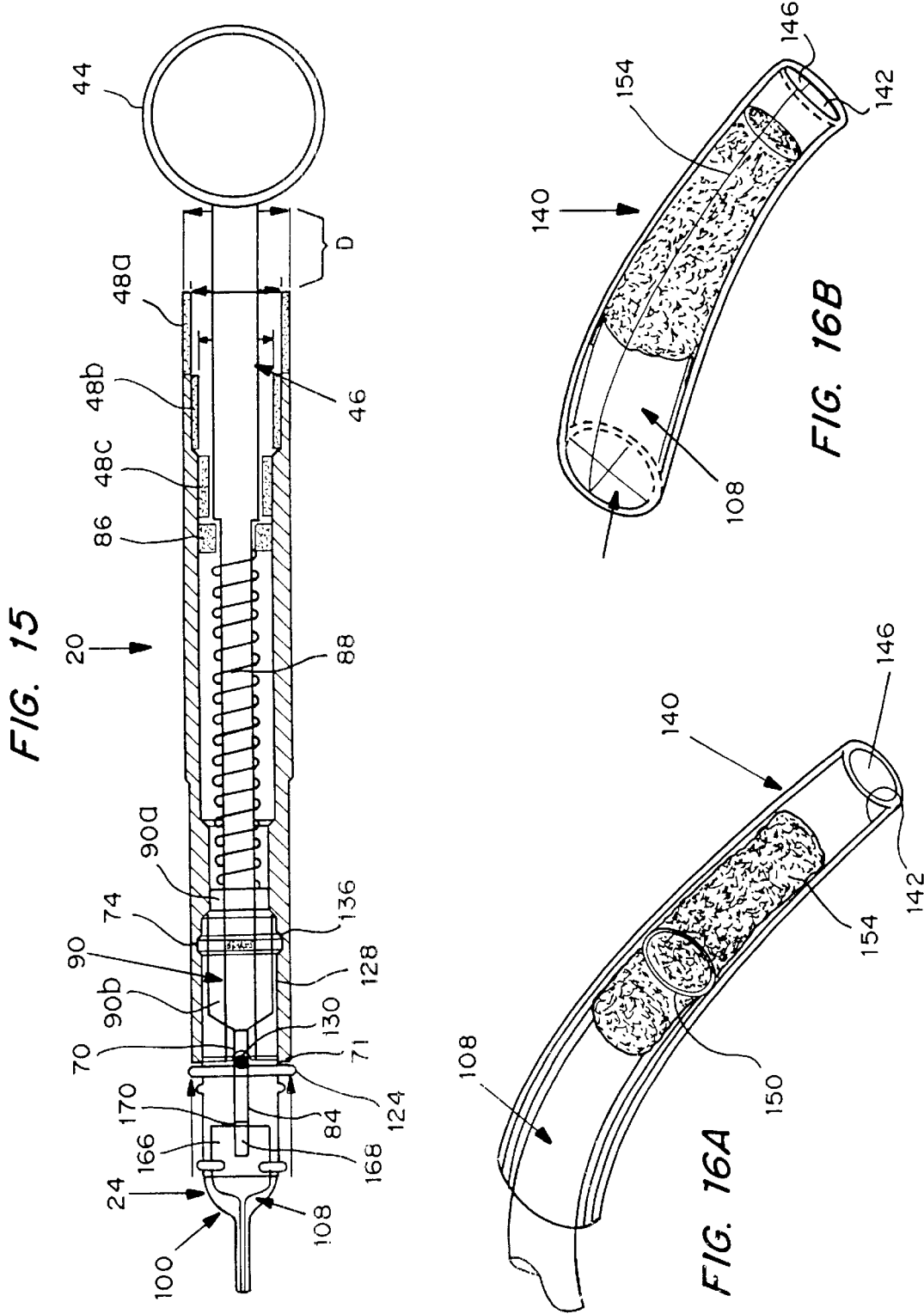

# DISPENSING APPARATUS AND CARTRIDGE

TECHNICAL FIELD

The present disclosure is directed to apparatus, components, and methods of treatment for periodontal disease.

BACKGROUND

Periodontal disease is an umbrella term for a variety of dental conditions associated with either gingivitis or periodontitis. Gingivitis is an inflammation of the gingiva, commonly known as gums, that is commonly associated with poor oral hygiene and/or the hormonal state of the patient. If left untreated, gingivitis may develop into periodontitis.

Periodontitis is a bacterial disease in which the infection has progressed to involve the oral tissues that retain the teeth in the jawbone. With this disease the gums become red and inflamed. This condition, if untreated, results in damage to the ligaments and bone holding the teeth in place, and formation of pockets around the teeth. As the pockets become deeper, teeth loosen, to a point where they may fall out. The severity of periodontitis is determined by dentists and other dental practitioners, by measuring the depth of these pockets and reviewing x-rays of the teeth and jawbone.

Periodontal disease involves a different treatment protocol than other oral diseases. While many oral diseases can be treated with proper hygiene, fluoride, pastes, washes and rinses, periodontal disease is often more refractile to treatment. This is because of differences between the oral and periodontal cavities. The oral cavity is essentially an aerobic environment, constantly perfused by saliva. In contrast, the periodontal cavity is more anaerobic, and is perfused by plasma filtrate, known as "crevicular fluid". The growth of microorganisms within the periodontal cavity microenvironment may cause periodontal disease. As the disease progresses, the periodontal microenvironment becomes more anaerobic, and the flow of crevicular fluid increases.

Efforts to treat periodontal disease have met with limited degrees of success. This is because the site of the bacterial infections in the periodontal cavity are largely inaccessible to agents present in the oral cavity as well as agents provided to the oral cavity, such as mouthwashes, rinses and the like. Moreover, the increased outflow of crevicular fluid that accompanies periodontal disease inhibits therapeutic agents placed into the oral cavity from entering the pockets.

Oral systemic administration of antibiotics has been shown to be a useful method of controlling subgingival flora. However, because of side effects, such as those of the digestive system, oral systemic administration has had only limited use in treating periodontal disease. Oral systemic therapy also requires frequent dosing, so patient compliance is frequently a problem.

Recently, efforts have focused on delivering therapeutic agents directly to these pockets, in some cases, in a controlled release formulation. In general, administration of agents directly to the pocket permits higher local drug concentrations that can be achieved by systemic administration. Also, some agents such as tissue growth factors must be administered directly to the target site, i.e., the periodontal pocket. Also, as these products are typically administered by dental professionals patient compliance is not of moment here.

U.S. Pat. No. 4,175,326 to Goodson discloses the use of a drug-filled polymer hollow fiber. The disclosed delivery system is tied around a tooth and gently pressed below the margin of the gingiva so that it resides in the periodontal pocket, and can deliver tetracycline for a prolonged period, such as a week or more.

Although these devices may be able to dispense and appropriate drug for a time span of a week or more, they have not been widely used. This is because their application is difficult and time consuming and the device may be dislodged by the patient during tooth brushing, flossing or eating.

The aforementioned disadvantages were overcome by administration of microparticles in dry form to the periodontal pocket by use of an apparatus disclosed in U.S. Pat. Nos. 5,236,355, 5,366,733 and 5,622,498, all to Brizzolara, et al., all three patents are incorporated by reference herein. These patents disclose treating dental diseases by administration of dry microparticles to the periodontal pocket. Microparticles suitable for this purpose may have compositions, as described in U.S. Pat. Nos. 5,000,886, 5,143,661 and 5,500,228, all to Lawter, et al., all three of these patents incorporated by reference herein, and U.S. Pat. Nos. 5,236,355, 5,366,733 and 5,622,498, all to Brizzolara, et al., and may be produced by the methods disclosed in the aforementioned six U.S. patents.

SUMMARY

The apparatus, components and methods disclosed herein improve on the contemporary art by providing a dispensing apparatus that can effectively deliver therapeutic agents directly to the periodontal pockets. The apparatus disclosed herein includes a reusable handle that is fitted with disposable cartridges, loaded with a composition, for example, a precise dose of a therapeutic agent. This saves the clinician time, eliminates guessing as to the proper dose, and reduces the amount of disposable instrumentation, making the process more economical. Additionally, the handle includes a body that has a configuration familiar to dental professionals, allowing them to use the disclosed apparatus with greater comfort and less training time. The cartridge provides for effective delivery of compositions, such as agents, as its tip is deformable, typically from a circular to an oval shape, either manually by the dental professional or upon contact with teeth or other tissues, whereby this flattened tip can penetrate deeply into pockets for quick and direct application of therapeutic agents.

An embodiment disclosed is directed to an apparatus for dispensing at least one material to a periodontal pocket. The apparatus has a barrel including a body portion and a tube portion, the tube portion extending from the body portion and including a tip configured for being deformed to at least one geometry different from its initial geometry. There is also a plunger, at least a portion of the plunger slideably housed within the barrel, the plunger configured for contacting a portion of an external force applying member. Additionally, there is a quantity of dry particles, for example a composition such as a therapeutic agent(s) or the like, and at least a portion of the dry particles are within the tip. A cap or closure member may be fitted over the tip to maintain the integrity of the composition until use is desired.

The apparatus is configured for receipt in an external force applying member, for example, a handle with a spring loaded shaft, in a temporarily locking arrangement. When use is desired, the apparatus snaps or locks into the handle and the spring loaded shaft is moved into contact with the plunger, pushing it, so as to push composition out of the tip into the periodontal pocket.

Another embodiment is directed to apparatus for dispensing material. This apparatus is formed of a barrel with a plunger, at least a portion of which is slideably housed in the barrel. The barrel includes a body portion and a tube portion, the tube portion extending from the body portion and including a tip configured for being deformed to at least one geometry different from its initial geometry. The plunger is configured for contacting a portion of an external force applying member.

The apparatus is configured for receipt in an external force applying member, for example, a handle with a spring loaded shaft, in a temporarily locking arrangement. When use is desired, the apparatus snaps or locks into the handle and the spring loaded shaft is moved into contact with the plunger in order to push it, to release a composition, previously loaded into at least the tip, out of the tip to the desired site.

Another embodiment is directed to a method for treating periodontal disease. This method involves providing an apparatus comprising, a force applying member adapted for receiving a barrel of a cartridge and a cartridge. The cartridge has a barrel including a body portion and a tube portion, the tube portion extending from the body portion, and the tube portion ends in a tip, that is configured for being deformed to at least one geometry different from its initial geometry. There is also a plunger, at least a portion of the plunger slideably housed within the barrel, the plunger configured for contacting a portion of the force applying member. There is also a quantity of dry particles, at least a portion of the dry particles being within the tip. The force applying member and cartridge are then placed into operative communication each other, for example, by a temporary locking engagement. The tip is then deformed, for example, to a substantially flattened geometry, and the deformed tip is moved into at least one periodontal pocket. The force applying member can have a portion of it (e.g., a spring-loaded shaft), moved to contact the plunger, moving the plunger so as to deliver the composition to the at least one periodontal pocket.

BRIEF DESCRIPTION OF THE DRAWINGS

Attention is now directed to the drawing figures, where like reference numerals or characters indicate corresponding or like components. In the drawings:

FIG. 2 is a cross sectional view of the sleeve of FIG. 1 with the finger rest removed;

FIG. 3 is a cross-sectional view of the shaft and associated components of FIG. 1;

FIG. 15 is a cross-sectional view of the apparatus of FIG. 1 with the cartridge in the locked position;

FIGS. 16A and 16B are perspective views of the tip of the apparatus of FIG. 1 during operation of the apparatus of FIG. 1;

DETAILED DESCRIPTION OF THE DRAWINGS

Figure 1:
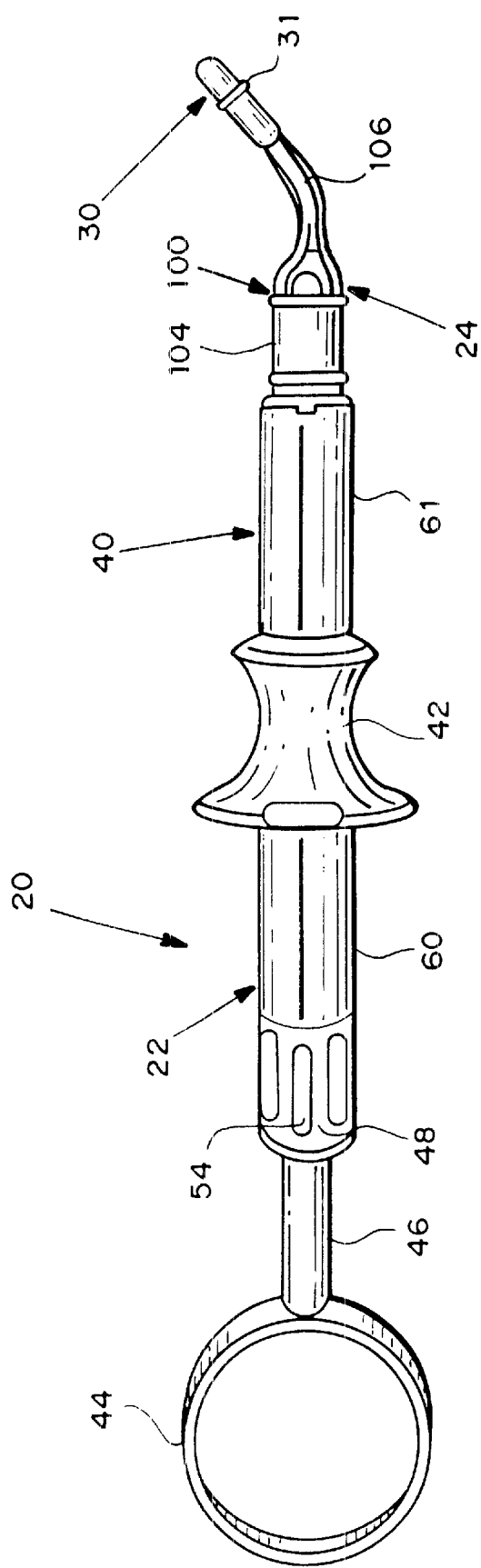
FIG. 1 is side view of the apparatus disclosed herein.

FIG. 1 shows an apparatus 20 formed from a handle 22 and a cartridge 24 that connects to the handle 22 and is separable therefrom. The cartridge 24 is typically disposable, and for example, is preloaded with a composition or substance, for example, a therapeutic agent(s) or the like, as detailed below. While a single cartridge 24 is shown, this cartridge 24 is exemplary only, as multiple cartridges are typically used one after the other in a typical procedure, as the therapeutic agent in each cartridge is exhausted. The end of the cartridge 24 is typically covered by a cap (or covering member) 30 (typically with a peripheral ring 31 to facilitate gripping by the dental professional) or other closing member, typically in a frictional engagement, that maintains the integrity of the composition in the cartridge 24 until actual use, when this cap 30 is removed.

The handle 22 is of a configuration and dimensions similar to other dental instrumentation. The handle 22 is formed of a sleeve 40, with a fingergrip 42 surrounding it. A thumb ring 44, connected to a spring loaded shaft 46, extends from the sleeve 40, with the shaft 46 held in place by a nut member 48, that includes a threaded portion 50 (FIG. 3) that connects to a correspondingly threaded portion 51 (FIG. 2) on the inner wall 52 (FIG. 2) of the sleeve 40. The nut member 48, on a proximal portion 48a (FIG. 3), includes a roughened, knurled or grooved outer surface 54, to assist the user in gripping, when opening the handle 22 is desired.

Turning also to FIGS. 2 and 3, the handle 22 is separated into the sleeve 40 (FIG. 2) and the shaft 46 and associated components (FIG. 3). The sleeve 40 includes a proximal end 60 and a distal end 61. The proximal end 60 includes a threaded portion 51 along its inner wall 52, for accommodating the correspondingly threaded portion 50 on an intermediate 48b portion of the nut member 48. Moving distally (in a direction away from the thumb ring 44), there is a section 64 for accommodating the spring 88 and its proximal confinement 86 and distal confinement 90, specifically its head 90a. This spring section 64 chamber includes a reduced diameter portion 66, that serves as a stop surface for the head 90a of the distal confinement 90, when the shaft 46 is pushed distally by the thumb ring 44.

The distal end 61 includes a notch (or indent) 70 at the outer edge 71 of the sleeve 40, for receiving a corresponding nub 130 (FIG. 4) on the cartridge 24, to prevent the cartridge 24 from rotating in the sleeve 40 (of the handle 22) when the cartridge 24 (in particular, its flanges 128, see FIG. 4) is locked in place in the handle 22, as detailed below. Proximal of this notch 70 is a chamber 72 for accommodating the flanges 128 of the cartridge 24 as pushed outward by the body 90b of the distal confinement 90. The chamber 72 terminates at a groove 74 that typically extends continuously around the inner wall 52 of the sleeve 40. The groove 74 is typically triangular in its edges 76, to accommodate the corresponding protrusions 136 (FIG. 4) on the flanges 128 (FIG. 4) of the cartridge 24, upon their seating therein, when the cartridge 24 is locked in the handle 22.

These triangular edges 76 allow for removal of the cartridge 24 from the handle 22, as the protrusions 136 of the flanges 128 can slide over these surfaces 76, allowing for the release of the cartridge 24, as detailed below. A section 80 for accommodating the body 90b of the distal confinement 90 is intermediate the groove 74 and the spring chamber 64.

The shaft 46 extends (in the distal direction) from the thumb ring 44 to the shaft end 84 (distal end). The nut member 48, proximal confinement 86, spring 88 and distal confinement 90 (formed of a head 90a and a body 90b) are all torroidal and slideable on the shaft 46. When the nut member 48 is attached to the sleeve 40 (so as to be fixed), in its normal operation, the nut member 48, at its distal portion 48c, serves as a confinement for the proximal confinement 86, when the shaft 46, typically via the thumb ring 44, is moved in the proximal direction (outwards with respect to the sleeve 40). The shaft 46 includes an outwardly extending ring 92 at its distal end 84. This ring 92, typically molded as part of the shaft 46, is fixed, and serves to limit distal movement of the distal confinement 90 for the spring 88.

Handle 22 and all components thereof, except the spring 88, is typically made of materials such as metals and in particular surgical grade steels, for example, 303 Stainless Steel. The spring 88 is typically made of metals such as surgical grade steels, and for example, stainless steels other then 303 Stainless Steel. Accordingly, the handle 22, including the spring 88, is sterilizable and reusable. Handle components may also be made by injection molding of suitable resins.

Figure 4:
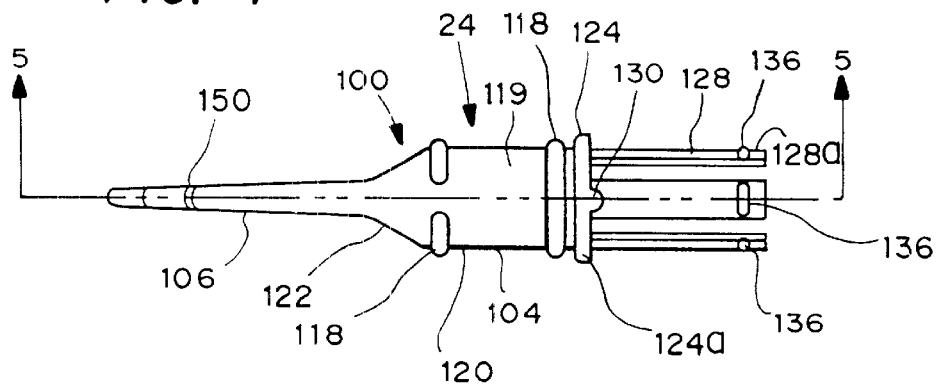
FIG. 4 is a top view of the cartridge of FIG. 1.
Figure 5A:
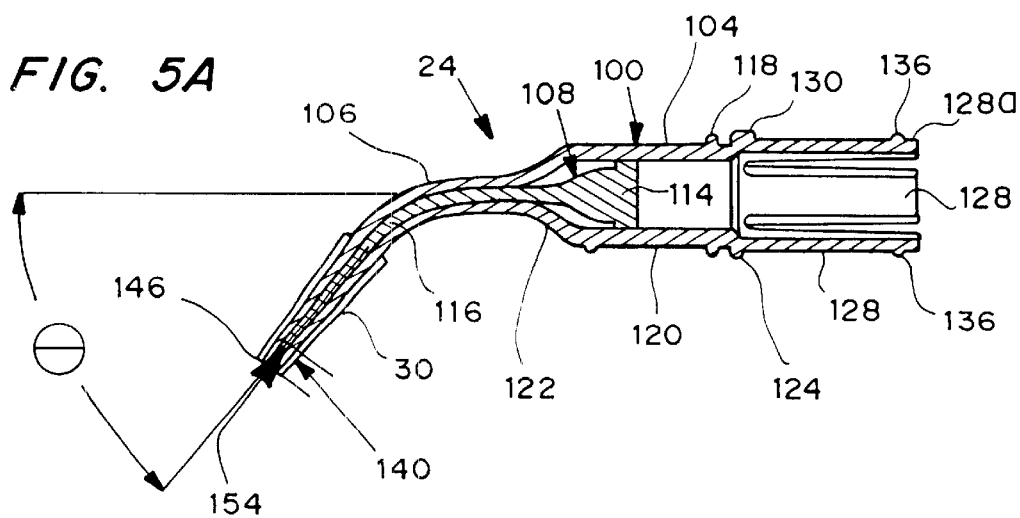
FIG. 5A is a cross-sectional view taken along line 5—5 of the cartridge of FIG. 4 with the plunger in a first position.
Figure 5B:
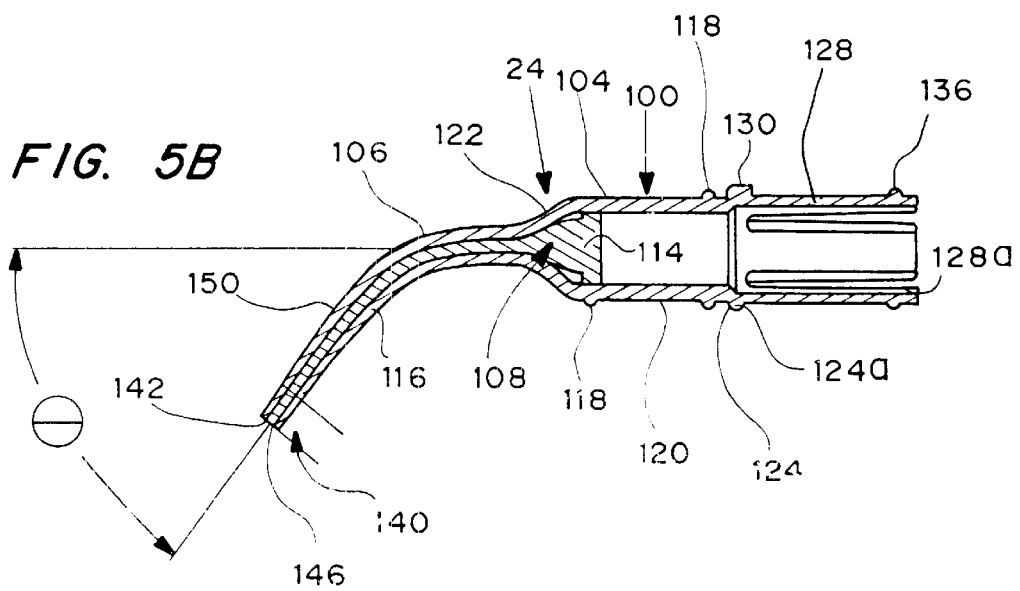
FIG. 5B is a cross-sectional view taken along line 5—5 of the cartridge of FIG. 4 with the plunger in a second position.

FIGS. 4, 5A and 5B show the cartridge 24, as formed of a barrel 100. The barrel 100 has a body portion 104 and a tube portion 106, in which a plunger 108 is fitted, for sliding therein. The plunger 108 includes a head 114 for movement within the body portion of the barrel 100, and a tail 116, for movement in the tube portion 106 of the barrel 100.

The tube portion 106 is typically angled, at an angle Θ, that is for example, approximately 40 to 60 degrees, and for example, in particular approximately 50 degrees, to provide the dental professional (clinician) with easy access to the periodontal pockets. The plunger 108, enclosed within the barrel 100 is curved similarly. There may be protrusions 118 on the outer surface 119 of the barrel 100, to provide a tactile indication of a gripping area for the cartridge 24.

The body portion 104 is typically a cylindrical segment 120, with an inwardly tapered portion 122 to the tube portion 106, and a collar 124, at the opposite end. Flanges 128 extend from the collar 124. The collar 124 has an inner diameter diameter less than the inner diameter of the sleeve 40 (between the inner walls 52a) of the handle 22, this collar inner diameter extending to an outer diameter that is greater than this sleeve, such that the collar surface 124a abuts the edge 71 of the sleeve 40, so as to limit movement of the cartridge 24, and in particular, prevent the cylindrical segment 120 from moving into the sleeve 40 of the handle 22. For example, the outer diameter of the collar 124 is equal to or slightly greater than the outer diameter of the sleeve 40 of the handle 22, such that the cartridge 24 and handle are flush along their outer surfaces.

A nub 130 protrudes from the collar 124. This nub 130 is correspondingly shaped, for example, semicircular here, with respect to the notch 70 in the handle 22, for seating therein, to prevent rotation of the cartridge 24. This nub 130 could also be any other shape provided that upon seating in the notch 70, typically correspondingly shaped, such that the seating will prevent rotation of the cartridge 24. The nub 130 is for example, positioned approximately 180 degrees with respect to the bending of the tube portion 106, for ease of access to the periodontal pocket by the dental professional. However, any other positioning is also suitable.

The flanges 128 extend from the collar 124. These flanges 128, based on the resilience of the material of the barrel 100, are flexible, and are designed to move radially outward and inward. Protrusions 136 extend from the outer surfaces 128a of each of the flanges 128. These protrusions 136 are typically rounded (but could also be triangular or any other shape that allows for sliding easily out of the grooves 74) and configured for seating into the groove 74 of the handle 22, so as to create a locking engagement of the cartridge 24 in the handle 22. Here, for example, four flanges 128 are shown in a cylindrical (rounded) a orientation, to correspond in shape to the sleeve 40 and distal confinement body 90b of the handle 22. However, any number of flanges 128 is suitable, provided the locking engagement of the cartridge 24 in the handle 22 can be attained.

Figure 5C:
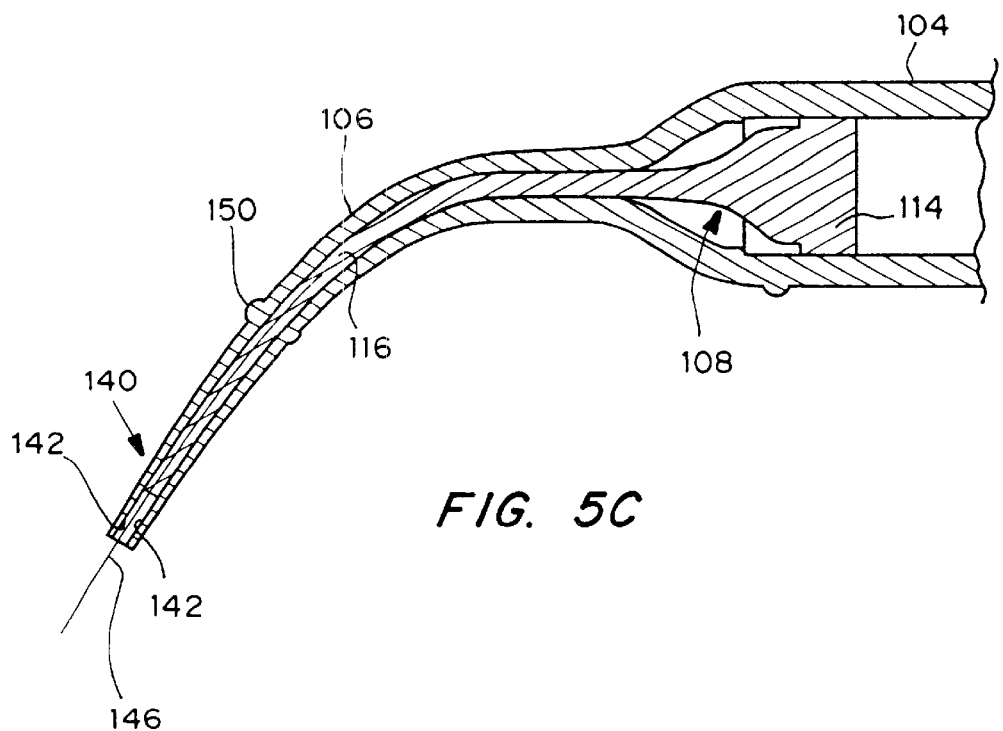
FIG. 5C is a cross-sectional view taken along line 5—5 of the cartridge of FIG. 4 with the plunger in a first position but lacking with the cap and composition removed.
Figure 6:
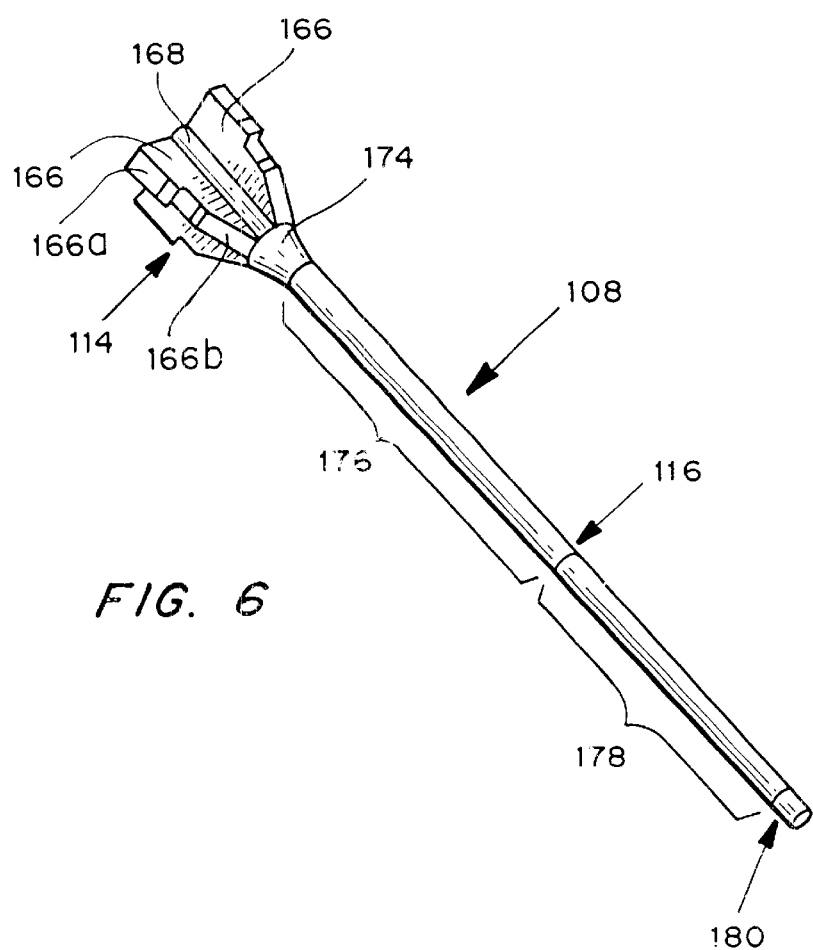
FIG. 6 is a perspective view of the plunger of the apparatus.
Figure 7:
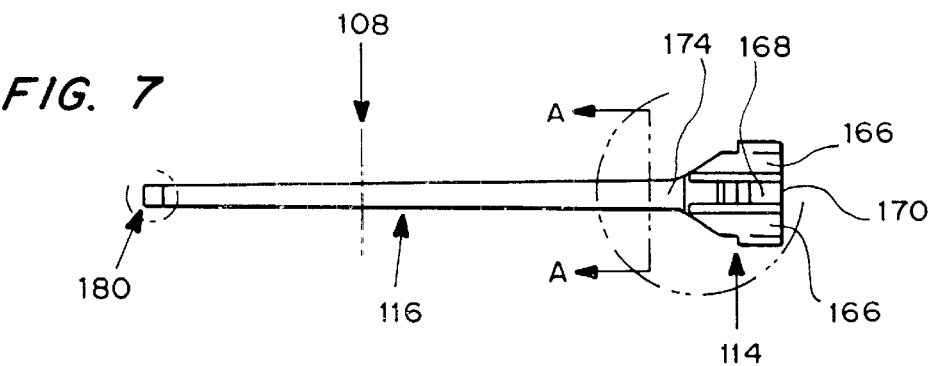
FIG. 7 is a cross-sectional view of the plunger of the apparatus.

Turning also to FIG. 5C, the tube portion 106 terminates at a tip 140, that tapers inward. This inward tapering (distally) provides the tip 140 with reduced inner wall 142 thickness, allowing the tip 140, with its initially circular opening 146 and cylinder shape, to change geometries, and flatten out, such that the opening 146 and the tip 140 deform, typically into an oval shape (in cross section) and thus, the tip 140 flattens. This changing in geometries is done by manual manipulation by the dental professional (prior to use) or upon contact with a tooth or other tissue. This flattening provides greater accessibility and maneuverability of the tip 140 in the periodontal pocket, as detailed below.

The tube portion 106 includes a ring protrusion 150 proximate the tip 140 that serves in frictionally retaining the cap 30 on the tube portion 106 (over the tip 140), prior to its removal, when use of the cartridge 24 is desired.

An amount of a composition 154 is typically placed (preloaded) into the tip 120 (and if necessary into the tube portion 106). This composition is typically a particulate composition, such as a dry microparticle composition in a sufficient treatment quantity. For example, the composition can be ARESTIN™ minocycline Hydrochloride (HCl) microspheres, from OraPharma, Inc., 732 Lewis Drive, Warminster, Pa. 18974, for example, in a 1 mg dosage, or those compositions as disclosed in U.S. Pat. Nos. 5,000,886, 5,143,661, 5,236,355, 5,366,733, 5,500,228, and 5,622,498, all six disclosures of which are incorporated by reference herein. These compositions can be dispersed in matricies of biocompatible and biodegradable polymers, in accordance with the disclosure of U.S. Pat. No. 5,622,498.

For example, dry microparticle compositions may include therapeutic agents, such as antibacterials, antibiotics, antiflugal agents, anti-inflammatory agents, immunosuppressive agents, immunostimulatory agents, dentinal desensitizers, odor masking agents, immune reagents, anesthetics, antiseptics, nutritional agents, antioxidants, lipopolysaccharide complexing agents, peroxides, tissue growth factors, or mixtures thereof. The therapeutic agent could also have antibiotic activity.

Exemplary therapeutic agents may be antibiotics such as tetracycline, a pharmaceutically acceptable salt of a tetracycline, hydrates of a tetracycline and hydrates of a pharmaceutically acceptable salt of a tetracycline. The tetracyclines may be doxycycline, a pharmaceutically acceptable salt of doxycycline, hydrates of doxycycline and hydrates of a pharmaceutically acceptable salt of doxycycline. Also, the tetracycline may be minocycline, a pharmaceutically acceptable salt of minocycline, hydrates of minocycline and hydrates of a pharmaceutically acceptable salt of minocycline.

These exemplary therapeutic agents are in the form of particles and in particular, dry particles. They can typically range from about 0.00001 to about 50 parts by weight per 100 parts by weight of the particles or from about 1 to about 50 parts by weight per 100 parts by weight of the particles, or more particularly from about 4 to about 40 parts by weight per 100 parts by weight of the particles.

For example, polymers for the aforementioned matricies may include polyglycolide, poly(l-lactide), poly(dl) lactide, poly (glycolide-co-lactide), poly (glycolide-co-dl lactide), poly (alpha hydroxybutyric acid, poly(orthoesters), poly (p-dioxanone) and mixtures thereof. The polymers can also be block copolymers of polyglycolide, trimethylene carbonate and polyethylene oxide.

These polymers may also be such that they become tacky upon contact with water.

The aforementioned particles of particulate compositions including therapeutic agents, may for example, have particles with diameters ranging from about 0.1 to about 1000 microns, and specifically, from about 10 to about 200 microns, and more specifically, from about 30 to about 120 microns.

The barrel 100 of the cartridge 24 is of, for example, as an integral unit, of, for example, polymers, such as olefin homopolymers or copolymers or mixtures thereof, such as polypropylene (e.g., MONTELL PD-626 Polypropylene), or polyethylene. It is typically formed by techniques such as injection molding or the like. The bending (curving) of the tube portion 106 is performed in a separate step, after the injection molding. The cap 30 is typically of a polymeric material such as polypropylene, and it may be colored, so it can be easily differentiated from the tube portion 106.

The plunger 108 is enclosed within the barrel 100, in a frictionally tight but slideable engagement. FIG. 5A details the plunger 108 in a first position, prior to use, while FIG. 5B details the plunger 108 in a second or post use position (after the plunger 108 has been pushed its requisite distance by the shaft 46 of the handle 22, as detailed below). The inwardly tapered portion 122 of the cylindrical section 120 serves as a travel limit for the plunger 108.

Turning to FIGS. 6–9, the plunger 108 is shown in detail. In these figures, the plunger 108 is shown straight and not bent or angled. This is for description purposes, as the plunger 108, when loaded into the barrel 100 will conform to the shape of the barrel 100.

The head 114 and tail 116 portions of the plunger 108 are correspondingly configured with respect to the body 104 and tube 106 portions of the barrel 100, where they reside.

Figure 8:
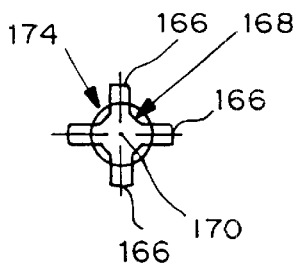
FIG. 8 is a rear view of the plunger of the apparatus.

Turning also to FIG. 8, the head portion 114 is formed of slats 166, typically with a discontinuous distal outer surface 166a, 166b. These slats 166 extend from a core 168, that has a central surface 170, typically flush with the proximal outer surfaces 166c of the slats 166. This central surface 170 is a contact surface for the distal end 84 of the shaft 46, that abuts it when movement of the plunger 108 to release composition 154 is desired. The head portion 114 slip fits into the body portion 104 of the barrel 100, resting loosely therein. The slats 166 prevent a gross misalignment of the central surface 170 and distal end 84 of the shaft 46. A trunk segment 174 of the head portion 114 serves as a limit of travel for the plunger 108 in the body portion 104 of the barrel 100 when the head portion 114 is pushed (distally) by the distal end 84 of the shaft 46.

The tail portion 116 extends from the trunk segment 174. The tail portion 116 includes a first segment 176, an intermediate segment 178 and an end segment (distal end segment) 180. The first segment 176 is tapered and thickened, for example, to have an outer diameter that provides the plunger 108 with strength while avoiding the tendency to bend (bow) or kink if excess pressure is applied by the shaft distal end 84 of shaft 46 of the handle 22. The intermediate segment 178 is of a lesser diameter less than or equal to that of the first segment 176.

Figure 9:
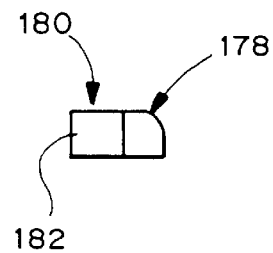
FIG. 9 is a cross sectional view of the end segment of the plunger of FIG. 7.

The end segment 180 is outwardly tapered (distally) to an edge surface 182, as shown in FIG. 9. This edge surface 182 is typically of a diameter greater, typically slightly greater, than the inner diameter of the tip 140, such that it contacts the inner walls 142 of the tip 140. This contact, typically is an interference fit, to provide the friction fit necessary to retain the plunger 108 in the barrel 100, while allowing the plunger 108 to slide in the barrel 100. It also allows for the composition 154 to be wiped cleanly off of the inner walls 142 of the tip 140, such that the composition is pushed (distally) out of the tip 140 (through the opening 146) to the treatment site, keeping the composition 154 from moving backwards (proximally) in the tube portion 106, or alternately keeping the composition from moving between the end segment 180 and inner walls 142 leading to jamming of the plunger 108.

The plunger 108 is typically an integral member, and made of materials such as polymers, for example, olefin homopolymers, olefin copolymers, and polycarbonate (e.g., Bayer® 2458-1117-Polycarbonate). The plunger 108 is formed by techniques such as injection molding or the like. The plunger 108 is typically of a polymer different than those polymers for the cartridge 24, so as to provide the plunger 108 with the ability to move smoothly between the aforementioned first (FIG. 5A) and second (FIG. 5B) positions.

Figure 10:
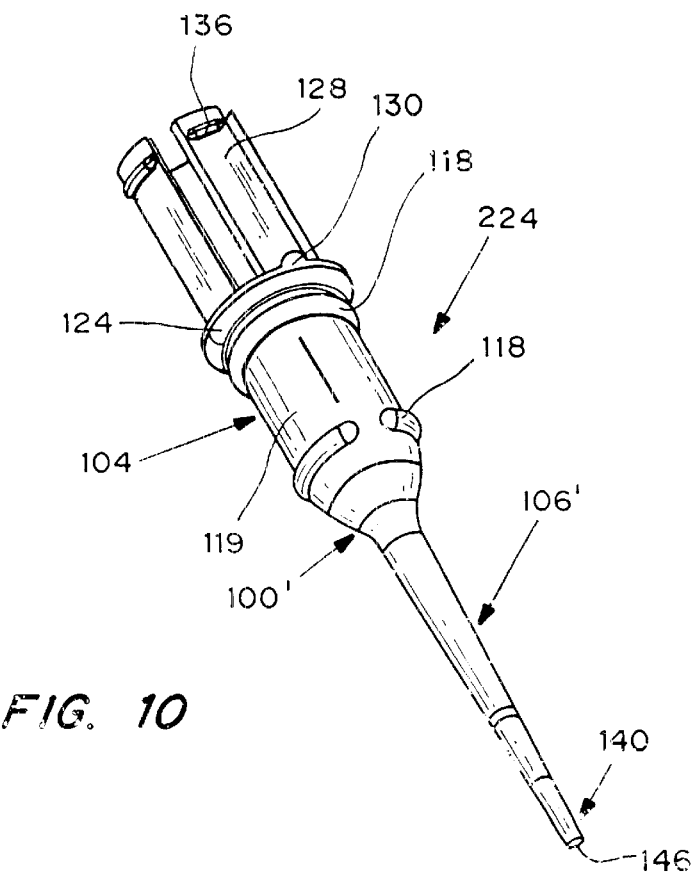
FIG. 10 is a perspective view of an alternate cartridge barrel for the apparatus of FIG. 1.
Figure 11:
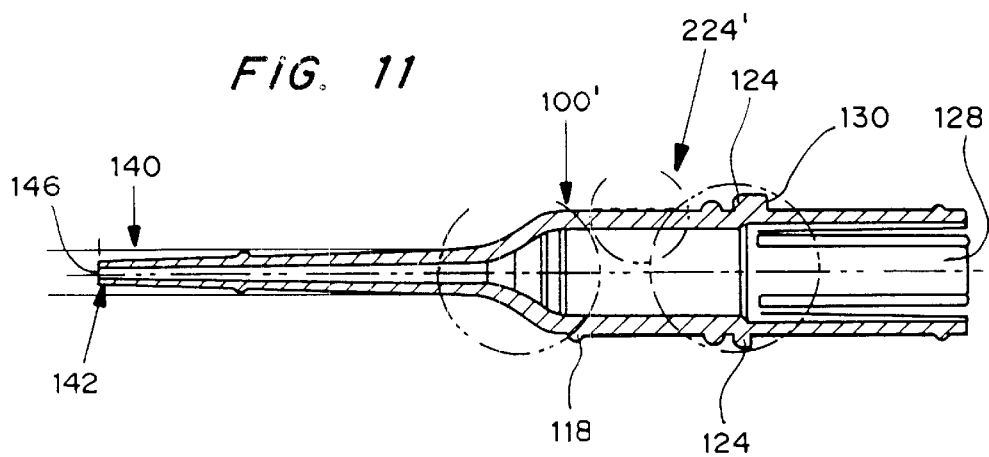
FIG. 11 is a cross-sectional view of the cartridge barrel of FIG. 10.

FIGS. 10 and 11 show an alternate embodiment of the cartridge 224, in particular the barrel portion 100' (the plunger is not shown). This embodiment is similar in all aspects to the cartridge 24 detailed above, except that the tube portion 106' (similar to tube portion 106) and the corresponding plunger are straight and not bent. All other aspects of construction and arrangement of components are similar to those detailed above and are thus, numbered similarly.

Figure 12:
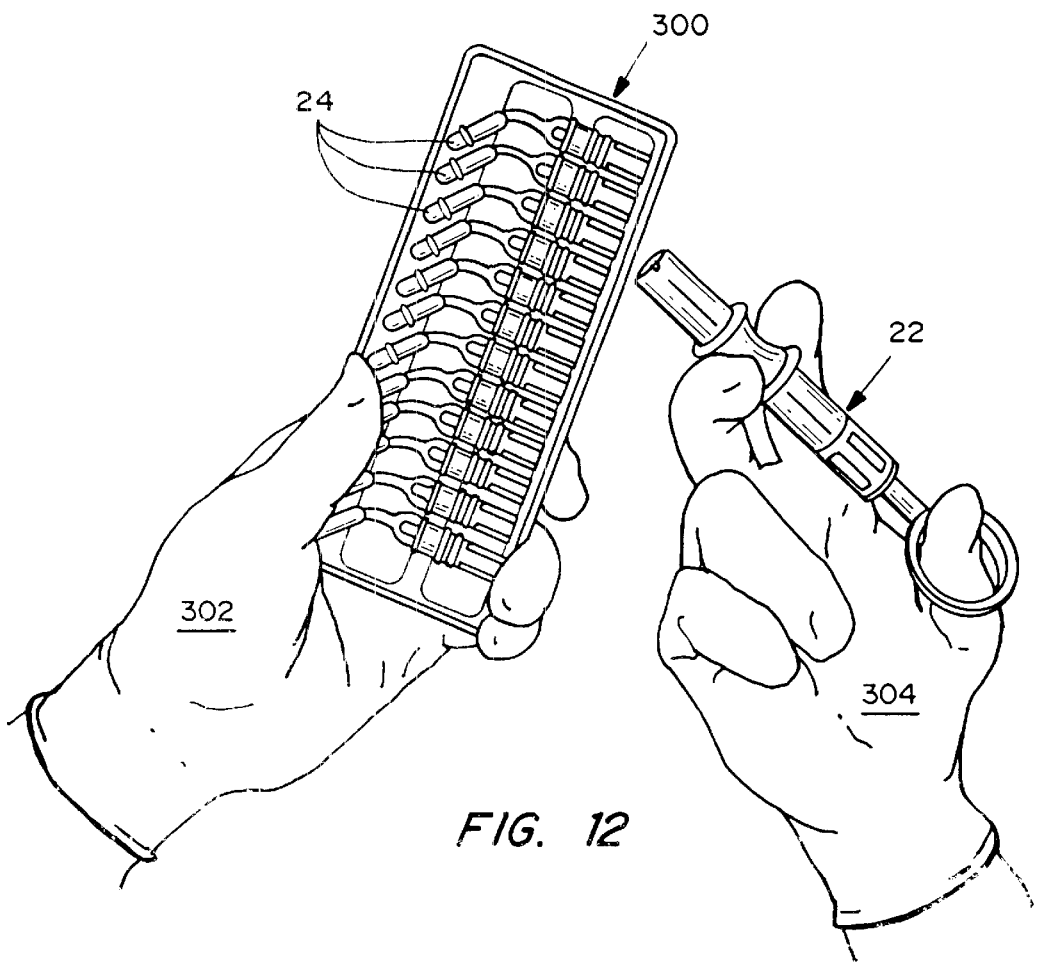
FIGS. 12–14 are perspective views detailing operation of the apparatus of FIG. 1.

FIGS. 12–20 detail exemplary operations of the apparatus 20. Initially, as shown in FIG. 12, multiple cartridges 24, for example twelve, are packaged in a tray 300. The tray 300 with cartridges 24 is typically packaged with desiccant in a heat-sealed foil laminated resealable pouch (not shown). The foil laminate for example, can be an aluminum or other foil laminate in accordance with the foil laminate disclosed in U.S. Pat. No. 5,622,498, incorporated by reference herein. The microparticles in each cartridge 24 may be provided in sterile form by aseptic manufacturing techniques or by terminal sterilization, for example, by gamma radiation, after being loaded into the respective cartridges 24 and packaged in a pouch.

Figure 13:
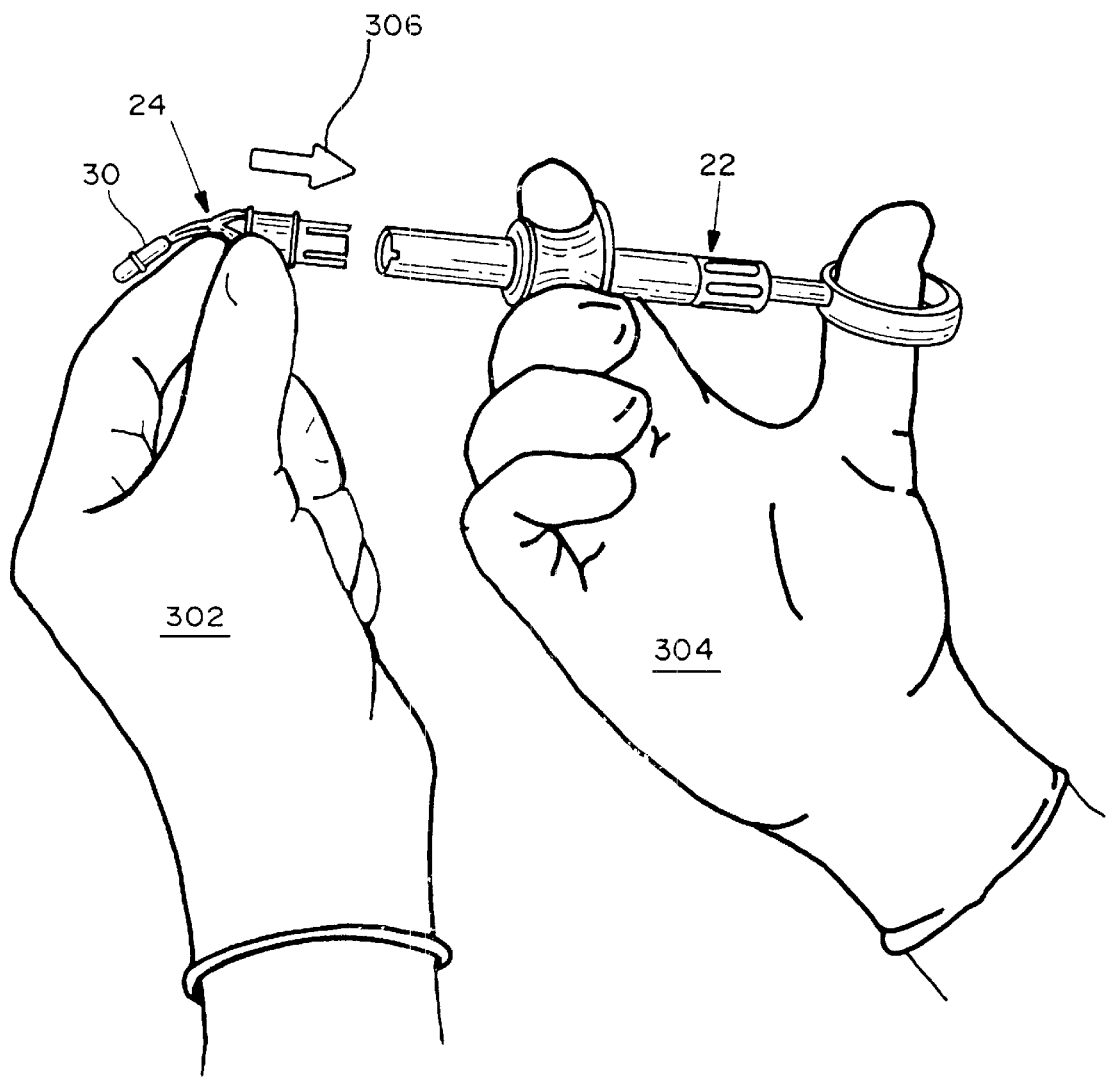
Figure 14:
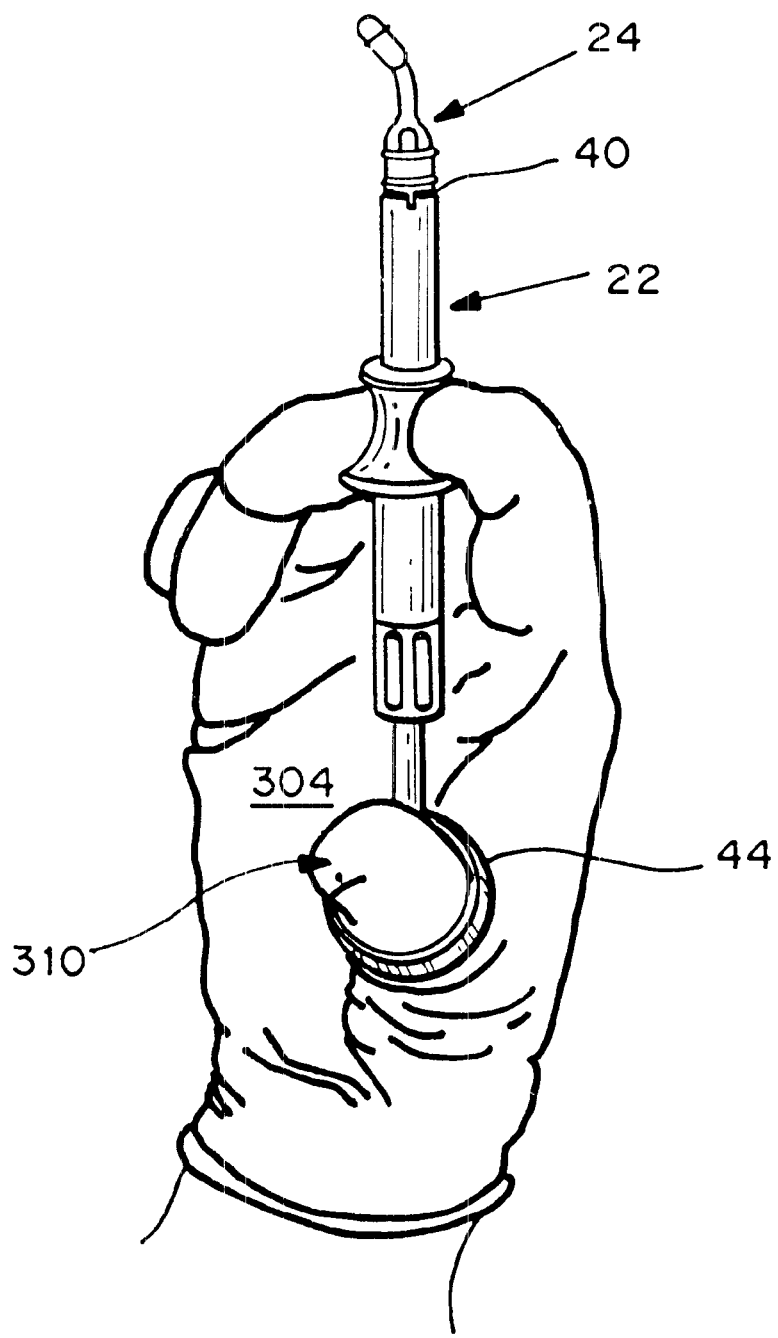

A first hand 302 of the dental professional grips the tray 300, while a second hand 304 grips the handle 22. A cartridge 24 is then removed from the tray 300, and moved in the direction of arrow 306 toward the handle 22, as shown in FIG. 13. Movement in the direction of arrow 306 continues until the cartridge 24 enters the sleeve 40 of the handle 22, defining the apparatus 20 and locks in place, as shown in FIG. 14. The handle 22 now rests comfortably in the hand 304 of the dental professional with the thumb 310 extending through the thumb ring and fingers 312 on the finger grip 42 for proper maneuvering. The cap 30 has now been removed.

Turning to FIG. 15, the locking of the cartridge 24 in the sleeve 40 is shown in detail. Here, the cartridge 24 has been pushed proximally, as the handle 22 remains at rest, as the thumb ring 44 is at the at rest distance D from the sleeve 40. The inward or proximal pushing of the cartridge 24 causes the flanges 128 to abut the body 90b of the distal confinement 90, whereby the flangesy 128 spread radially outward. Inward movement continues, until the nub 130 seats in the notch 70 (inward movement is made with nub 130 and notch in alignment) and the protrusions 136 engage the groove 74. This is typically noticed tactilely as well as an auditory "click" can be detected.

Additionally, the plunger 108 aligns with the shaft end 84, whereby the shaft end 84 contacts the central surface 170. The plunger 108 is in the first position, as shown in FIG, 5A. Throughout this attachment process, distal resistance is provided by the spring 88. Locking of the cartridge 24 is complete, as the nub 130 is seated in the notch 70, the collar 124 is close to or in abutment with the edge 71 of the sleeve 40, and the protrusions 136 of the flanges 128 are seated in the groove 74.

The tip 140, with the composition 154 therein, is in its normal or at rest geometry, with a circular or substantially circular opening and cross section, as shown in FIG. 16A. The dental professional can now manually deform the tip 140, typically by flattening it with an instrument. This flattening results in the opening 146 and the tip 140 having oval or flattened shape (and geometry), as shown to in FIG. 16B.

Figure 17:
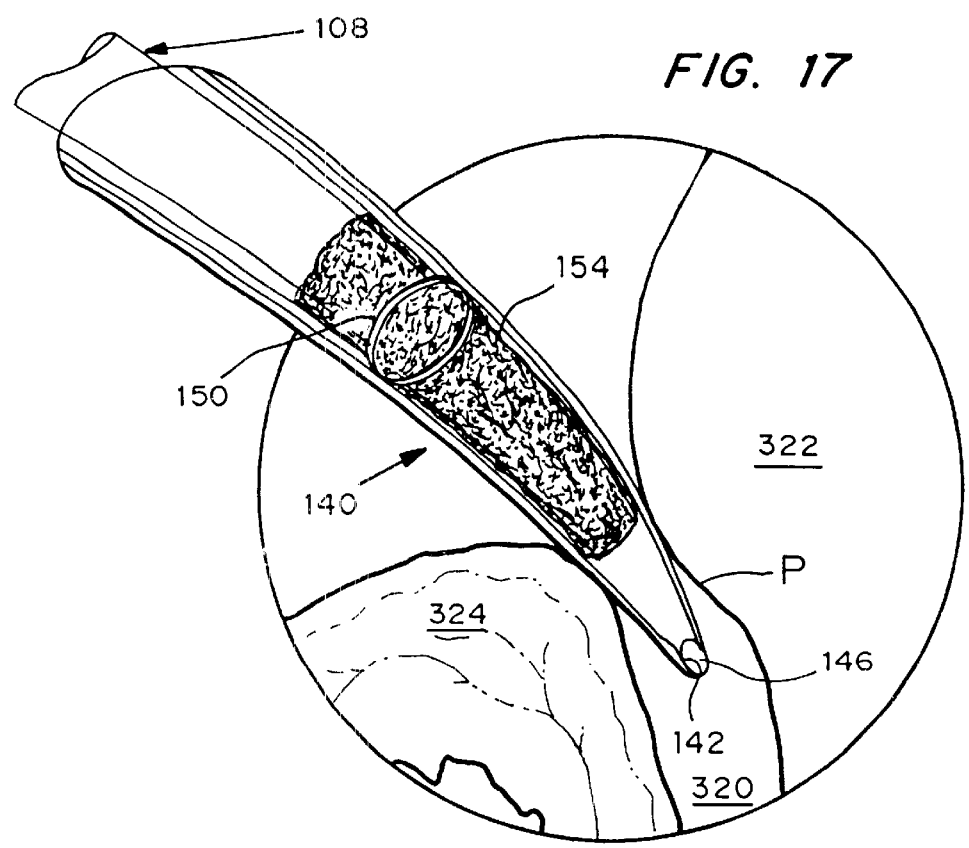
FIG. 17 is a perspective view of the cartridge with a flattened tip of the apparatus of FIG. 1 entering a periodontal pocket in operation.

The dental professional, familiar with thumb ring handle devices, can now maneuver the apparatus 20, in particular the tip 140 of the tube portion 106 of the cartridge 24 of the apparatus 20 to the periodontal pocket 320, between the tooth 322 and gum 324, as shown in FIG. 17. Here, the tip 140, that is now flattened, can be maneuvered deep into the periodontal pocket 320 (for emphasis, being the mark labeled P), between the tooth 322 and gum 324.

Figure 18:
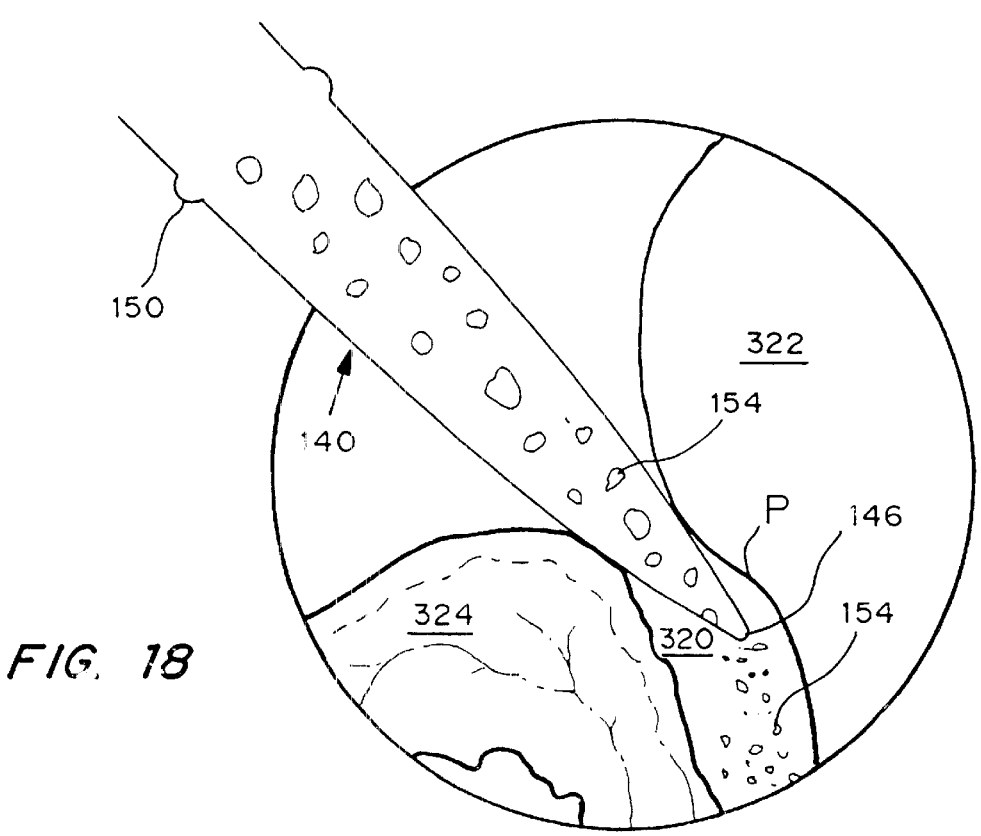
FIG. 18 is a view of the tip of the cartridge in a periodontal pocket, the tip exaggerated to illustrate operation of the apparatus of FIG. 1.

In FIG. 18, the composition 154 can now be released into the pocket. Here, turning also to FIG. 15, the thumb ring 44 is moved distally (toward the sleeve 40), such that the shaft 46 and distal tip 84 thereof moves distally, forcing the plunger 108 distally, ultimately to the second position shown in FIG. 5B, to force composition 154 out of the tip 140 through the opening 146 and into the pocket 320.

Figure 19:
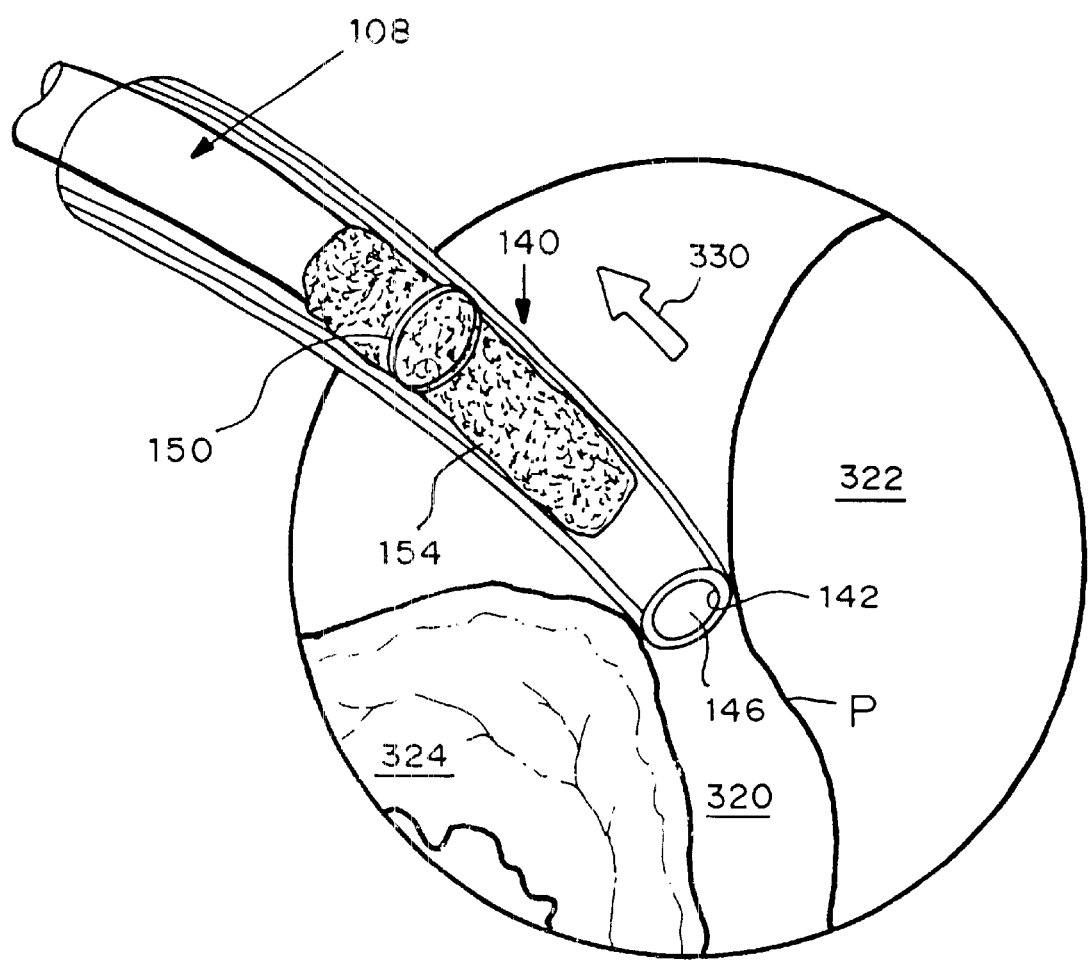
FIG. 19 is an alternate operation for the cartridge of the apparatus of FIG. 1, where the tip is deformed upon contact with the teeth or surrounding tissues.

Alternately, returning to FIG. 16A and its accompanying description, the dental professional can maneuver the apparatus 20 so as to abut the tooth 322 or gum 324, as shown in FIG. 19. This abutment, typically coupled with movement into the periodontal pocket 320 will cause the tip 140 to deform its shape, becoming flatter, to reach deeper into the periodontal pocket 320 (beyond the mark labeled P), as shown in FIG. 17. The process continues, as described for FIGS. 17 and 18 above.

Returning to FIG. 18, for both operations, with the cartridge 24, and in particular the tip 140, exhausted of composition 154, the apparatus 20 is manipulated, such that the cartridge is removed from the periodontal pocket 320, in the direction of the arrow 330.

Figure 20:
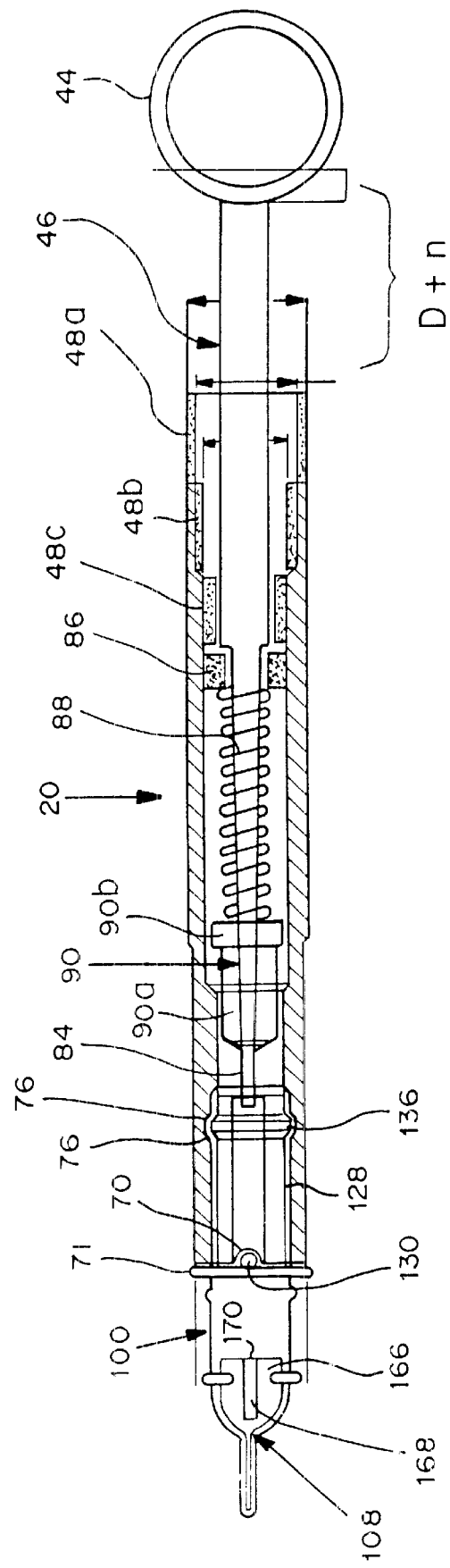
FIG. 20 is a cross-sectional view of the apparatus of FIG. 1 with the cartridge being unlocked for its removal from the handle.

Attention is now directed to FIG. 20. Here, the cartridge 24 has been exhausted as the plunger 108 is in the second position, as shown in FIG. 5B above. The spring 88 has caused the distal end 84 of the shaft 46 to move out of contact with the central surface 170 of the plunger 108, as the distal end 84 moves proximally toward the thumb ring 44, and return to the at rest position of the handle 22.

The thumb ring 44 is pulled proximally (away from the sleeve 40), a distance D plus an additional distance n, expressed D+n. The spring 88 is compressed, as this proximal pulling takes the body 90b of the distal confinement 90 out of abutting contact with the flanges 128, allowing them to spring back, moving radially inward, to their rest or normal positions. The protrusions 136 of the flanges 128 no longer seat in the groove 74, but rather just slightly extend into the groove 74. This allows for easy manual removal of the cartridge 24 from the handle 22, while the cartridge 24 is retained in an engagement with the handle 22, should the handle 22 be pointed downward, so the cartridge 24 remains in and does not fall out of the handle 22. This ease in removal is accomplished as the rounded edges of the protrusions 136, coupled with the triangular edges 76 of the grove 74, allow for the cartridge 24 to be easily pulled out of the sleeve 40 with minimal force. Once the cartridge 24 is removed from the handle 22, the process may be repeated with additional cartridges for as long as desired.

While preferred embodiments of an apparatus, components and methods, have been described above, the description of the apparatus, components and methods above is exemplary only. Those skilled in the art will recognize, or be able to ascertain using no more than routine experimentation, many equivalents to the specific embodiments of the invention described herein. Such equivalents are intended to be encompassed by the following claims.

What is claimed is:

1. An apparatus for dispensing at least one material to a periodontal pocket comprising:
    a barrel including a body portion and a tube portion, the body portion including flexible flanges for forming a temporary locking engagement with at least a portion of an external force applying member, the tube portion extending from the body portion and including a tip configured for being deformed to at least one geometry different from its initial geometry;
    a plunger, at least a portion of the plunger slidably housed within the barrel, the plunger configured for contacting a portion of an external force applying member; and
    a quantity of dry particles, at least a portion of the dry particles within the tip.

2. The apparatus of claim 1, wherein the dry particles comprise at least one therapeutic agent.

3. The apparatus of claim 2, wherein the dry particles comprise an effective amount of the at least one therapeutic agent, the therapeutic agent dispersed in a dry matrix comprising a biocompatible and biodegradable polymer.

4. The apparatus of claim 3, wherein the polymer is selected from the group consisting of polyglycolide, poly(l-lactide), poly(dl) lactide, poly (glycolide-co-lactide), poly (glycolide-co-dl lactide), poly (alpha hydroxybutyric acid, poly(orthoesters), poly (p-dioxanone) and mixtures thereof.

5. The apparatus of claim 3, wherein the polymer comprises a block copolymer of polyglycolide, trimethylene carbonate and polyethylene oxide.

6. The apparatus of claim 3, wherein the polymer becomes tacky upon contact with water.

7. The apparatus of claim 2, wherein the therapeutic agent is selected from the group consisting of an antibacterial, an antibiotic, an anti-inflammatory agent, an immunosuppressive agent, an immunostimulatory agent, a dentinal desensitizer, an odor masking agent, an immune reagent, an anesthetic, an antiseptic, a nutritional agent, an antioxidant, a lipopolysaccharide complexing agent, a peroxide, a tissue growth factor and mixtures thereof.

8. The apparatus of claim 2, wherein the therapeutic agent has antibiotic activity.

9. The apparatus of claim 8, wherein the therapeutic agent comprises an antibiotic selected from the group consisting of a tetracycline, a pharmaceutically acceptable salt of a tetracycline, hydrates of a tetracycline and hydrates of a pharmaceutically acceptable salt of a tetracycline.

10. The apparatus of claim 9, wherein the therapeutic agent comprises a tetracycline is selected from the group consisting of doxycycline, a pharmaceutically acceptable salt of doxycycline, hydrates of doxycycline and hydrates of a pharmaceutically acceptable salt of doxycycline.

11. The apparatus of claim 9, wherein the therapeutic agent comprises tetracycline is selected from the group consisting of minocycline, a pharmaceutically acceptable salt of minocycline, hydrates of minocycline and hydrates of a pharmaceutically acceptable salt of minocycline.

12. The apparatus of claim 2, wherein the therapeutic agent comprises from about 0.00001 to about 50 parts by weight per 100 parts by weight of the particles.

13. The apparatus of claim 12, wherein the therapeutic agent comprises from about 1 to about 50 parts by weight per 100 parts by weight of the particles.

14. The apparatus of claim 13, wherein the therapeutic agent comprises from about 5 to about 40 parts by weight per 100 parts by weight of the particles.

15. The apparatus of claim 1, wherein the particles have a diameter of from about 0.1 to about 1000 microns.

16. The apparatus of claim 15, wherein the particles have a diameter of from about 10 to about 200 microns.

17. The apparatus of claim 16, wherein the particles have a diameter of from about 30 to about 120 microns.

18. The apparatus of claim 1, wherein the barrel comprises a polymer selected from the group consisting of olefin homopolymers, olefin copolymers and mixtures thereof.

19. The apparatus of claim 18, wherein the olefin homopolymers or copolymer comprises a polymer selected from the group consisting of polyethylene and polypropylene.

20. The apparatus of claim 1, wherein the plunger comprises a polymer selected from the group consisting of olefin homopolymers, olefin copolymers and polycarbonates.

21. The apparatus of claim 2, wherein the at least one therapeutic agent includes minocycline Hydrochloride.

22. The apparatus of claim 1, wherein the body portion includes at least one nub for receipt in a correspondingly configured indent in at least a portion of an external force applying member to prevent the barrel from rotating.

23. The apparatus of claim 22, additionally comprising:
an external force applying member.

24. The apparatus of claim 23, wherein the external force applying member includes a handle.

25. The apparatus of claim 24, wherein the handle includes:
a sleeve including an indent for engaging the at least one nub of the barrel;
a spring-loaded shaft housed at least partially within the sleeve;
the sleeve and the shaft configured to engage a at least a portion of each of the flexible flanges of body potion of the barrel.

26. The apparatus of claim 25, wherein the spring-loaded shaft includes:
a proximal end and a distal end; and
a thumb ring at the proximal end.

27. The apparatus of claim 1, additionally comprising:
a removable closure confined for covering at least a portion of the tip to maintain the integrity of the dry particles.

28. The apparatus of claim 1, enclosed in a package.

29. The apparatus of claim 28, wherein the package comprises an aluminum-laminate pouch.

30. The apparatus of claim 28, wherein the package is resealable.

31. The apparatus of claim 1, enclosed in a sterilizable package.

32. The apparatus of claim 31, wherein the sterilizable package comprises an aluminum-laminate pouch.

33. The apparatus of claim 1, wherein the barrel and the plunger are formed of radiation sterilizable materials.

34. An apparatus for dispensing material comprising:
a barrel including a body portion and a tube portion, the body portion including flexible flanges for forming a temporary locking engagement with at least a portion of an external force applying member the tube portion extending from the body portion and including a tip configured for being deformed to at least one geometry different from its initial geometry; and
a plunger, at least a portion of the plunger slideably housed within the barrel, the plunger configured for contacting a portion of an external force applying member.

35. The apparatus of claim 34, wherein the body portion includes at least one nub for receipt in a correspondingly configured indent in at least a portion of an external force applying member to prevent the barrel from rotating.

36. The apparatus of claim 35, additionally comprising:
an external force applying member.

37. The apparatus of claim 36, wherein the external force applying member includes a handle.

38. The apparatus of claim 37, wherein the handle includes:
a sleeve including an indent for engaging the at least one nub;
a spring-loaded shaft housed at least partially within the sleeve;
the sleeve and the shaft configured to engage a at least a portion of each of the flexible flanges of body potion of the barrel.

39. The apparatus of claim 38, wherein the spring-loaded shaft includes:
a proximal end and a distal end; and
a thumb ring at the proximal end.

40. A method for treating dental disease comprising:

providing an apparatus comprising:
- a force applying member adapted for receiving a barrel of cartridge;
- a cartridge comprising:
  - a barrel including a body portion and a tube portion, the tube portion extending from the body portion and including a tip configured for being deformed to at least one geometry different from its initial geometry;
  - a plunger, at least a portion of the plunger slideably housed within the barrel, the plunger configured for contacting a portion of the force applying member; and
  - a quantity of dry particles, at least a portion of the dry particles within the tip;

placing the force applying member into operative communication with the cartridge;

deforming the tip to a substantially flattened geometry, and moving the deformed tip into at least one periodontal pocket.

41. The method of claim 40, additionally comprising:

delivering the particles to the at least one periodontal pocket.

42. The method of claim 41, wherein delivering the particles to the periodontal pocket includes, moving the at least a portion of the force applying member to move the plunger, and releasing the particles from the tip.

43. The method of claim 40, wherein the tip is deformed manually.

44. The method of claim 40, wherein the tip is deformed upon contact with a tooth or other tissue.

* * * * *

UNITED STATES PATENT AND TRADEMARK OFFICE
CERTIFICATE OF CORRECTION

PATENT NO. : 6,682,348 B2
DATED : January 27, 2004
INVENTOR(S) : Lawter et al.

It is certified that error appears in the above-identified patent and that said Letters Patent is hereby corrected as shown below:

Column 2,
Line 5, should read -- Although these devices may be able to dispense an --

Column 3,
Line 32, should read -- tive communication with each other, for example, by a temporary --
Line 59, should read -- lacking the cap and with the composition removed; --

Column 5,
Line 38, should read -- 88, are typically made of materials such as metals and in --
Line 65, should read -- diameter less than the inner diameter of the sleeve --

Column 6,
Line 14, should read -- the notch 70, typically correspondingly shaped, the --
Line 30, should read -- shown in a cylindrical (rounded) a orientation, to correspond --
Line 52, should read -- (preloaded) into the tip 140 (and if necessary into the tube --
Line 56, should read -- can be ARESTIN$^{TM}$ minocycline hydrochloride (HCI) --
Line 62, should read -- herein. These compositions can be dispersed in matrices of --

Column 7,
Line 1, should read -- fungal agents, anti-inflammatory agents, immunosuppressive --
Lines 26-30, should read -- For example polymers for the aforementioned matrices may include polyglycolide, poly(l-lactide), poly(dl-lactide), poly(glycolide-co-lactide), poly(glycolide-co-dl-lactide), poly(alpha hydroxybutyric acid), poly(orthoesters), poly(p-dioxanone) and mixtures thereof. The polymers can also --

Column 9,
Line 23, should read -- thumb ring 44 is at the "at rest" distance D from the sleeve 40. --
Line 26, should read -- ment 90, whereby the flanges 128 spread radially outward. --
Line 28, should read -- notch 70 (inward movement is made with nub 130 and notch 70 --
Line 34, should read -- The plunger 108 is in the first position, as shown in -- FIG. 5A. --
Line 47, should read -- an oval or flattened shape (and geometry), as shown in FIG. --
Line 61, should read -- 46 and distal tip 84 thereof move distally, forcing the --

UNITED STATES PATENT AND TRADEMARK OFFICE
CERTIFICATE OF CORRECTION

PATENT NO. : 6,682,348 B2
DATED : January 27, 2004
INVENTOR(S) : Lawter et al.

It is certified that error appears in the above-identified patent and that said Letters Patent is hereby corrected as shown below:

Column 10,
Line 18, should read -- 44, and returns to the "at rest" position of the handle 22.
Line 34, should read -- groove 74, allow for the cartridge 24 to be easily pulled out --

Column 11,
Lines 3-4, should read -- poly(dl-lactide), poly(glycolide-co-lactide),poly(glycolide-co-dl-lactide), poly(alpha hydroxybutyric acid). --
Line 13, should read -- antibiotic, an antifungal agent, an anti-inflammatory agent, an immunosuppres- --
Line 28, should read -- agent comprises a tetracycline selected from the group --
Line 33, should read -- agent comprises tetracycline is selected from the group --
Line 63, should read -- therapeutic agent includes minocycline hydrochloride. --

Column 12,
Line 11, should read -- the sleeve and the shaft configured to engage at least a --
Line 12, should read -- portion of each of the flexible flanges of the body portion of --
Line 20, should read -- a removable closure configured for covering at least a --
Line 38, should read -- of an external force applying member, the tube portion --
Line 61, should read -- the sleeve and the shaft configured to engage at least a --
Line 62, should read -- portion of each of the flexible flanges of the body portion of --

Column 13,
Line 4, should read -- of a cartridge; --

Column 14,
Line 1, should read -- deforming the tip to a substantially flattened geometry; --

Signed and Sealed this

Thirteenth Day of July, 2004

JON W. DUDAS
*Acting Director of the United States Patent and Trademark Office*